US00PP25884P2

(12) United States Plant Patent
Ault

(10) Patent No.: US PP25,884 P2
(45) Date of Patent: Sep. 8, 2015

(54) ***PHLOX* PLANT NAMED 'VIOLET PINWHEELS'**

(50) Latin Name: ***Phlox* hybrid**
Varietal Denomination: Violet Pinwheels

(71) Applicant: James R. Ault, Libertyville, IL (US)

(72) Inventor: James R. Ault, Libertyville, IL (US)

(73) Assignee: CHICAGOLAND GROWS, INC., Glencoe, IL (US)

( * ) Notice: Subject to any disclaimer, the term of this patent is extended or adjusted under 35 U.S.C. 154(b) by 112 days.

(21) Appl. No.: 13/998,931

(22) Filed: Dec. 24, 2013

(51) Int. Cl.
*A01H 5/00* (2006.01)

(52) U.S. Cl.
USPC ..... Plt./320

(58) Field of Classification Search
USPC ..... Plt./320
See application file for complete search history.

*Primary Examiner* — Susan McCormick Ewoldt
(74) *Attorney, Agent, or Firm* — Penny J. Aguirre

(57) ABSTRACT

A new cultivar of *Phlox* plant, 'Violet Pinwheels', that is characterized by its low spreading mounded plant habit, its blooming period for four to six weeks from early to mid-April to mid-May, followed by a light repeat blooming period from August through October, in northern Illinois, its slightly cupped flowers with turned in petals that are obovate in shape with a strongly constricted base and a broad rounded tip with a slight terminal notch, its flowers that at anthesis are vivid purple in color with light violet eyes and basal pairs of violet striae and age to a vivid violet color, its soft, needle-like foliage that is dark green in color, and its resistance to powdery mildew.

2 Drawing Sheets

Botanical classification: *Phlox* hybrid.
Cultivar designation: 'Violet Pinwheels'.

BACKGROUND OF THE INVENTION

The present invention relates to a new and distinct cultivar of *Phlox* plant, botanically of hybrid origin and known as *Phlox* 'Violet Pinwheels' and will be referred to hereafter by its cultivar name, 'Violet Pinwheels'. The new cultivar represents a new herbaceous perennial grown for landscape use.

The new invention arose from an ongoing controlled breeding program by the Inventor in Glencoe, Ill. The objectives of the breeding program are to develop improved cultivars of spring blooming moss phlox by developing select interspecific hybrids of *Phlox* with novel traits of flower colors, plant habits, and tolerance to drought and soils with high salinity and pH.

'Violet Pinwheels' was derived from a cross made in May of 2008 under controlled conditions (that excluded natural pollinators) between an unnamed plant of *Phlox bifida* as the female parent and *Phlox kelseyi* 'Lemhi Purple' (not patented) as the male parent. The resulting seedlings were planted for evaluation in June of 2009. 'Violet Pinwheels' was selected in April of 2010 as a single unique plant amongst the resulting seedlings.

Asexual propagation of the new cultivar was first accomplished by stem tip cuttings by the Inventor in May of 2010 in Glencoe, Ill. Asexual propagation by stem tip cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Violet Pinwheels' as a unique cultivar of *Phlox*.

1. 'Violet Pinwheels' exhibits a low spreading mounded plant habit.
2. 'Violet Pinwheels' blooms for four to six weeks from early to mid-April to mid-May, followed by a light repeat bloom from August through October, in northern Illinois.
3. 'Violet Pinwheels' exhibits slightly cupped flowers with turned in petals that are obovate in shape with a strongly constricted base and a broad rounded tip with a slight terminal notch.
4. 'Violet Pinwheels' exhibits flowers that at anthesis are vivid purple in color with light violet eyes and basal pairs of violet striae, flowers age to a vivid violet color.
5. 'Violet Pinwheels' exhibits soft, needle-like foliage that is dark green in color.
6. 'Violet Pinwheels' has been observed to be resistant to powdery mildew.

The female parent of 'Violet Pinwheels', an unnamed plant of *Phlox bifida,* differs from 'Violet Pinwheels' in having white flowers that are held flat, in having deeply notched petals, and in having darker violet striae at the base of each petal. The male parent of 'Violet Pinwheels', 'Lemhi Purple', differs from 'Violet Pinwheels' in having flower petals that are weakly obovate in shape with pointed apices, in having floral eyes that are white in color with no visible striae, and in having a very low creeping mat plant habit that is shorter in height. There are no cultivars that are of *Phlox bifida*×*Phlox kelseyi* known to the inventor. 'Violet Pinwheels' can also be most closely compared to the cultivars *Phlox bifida* 'Betty Blake' (not patented) and *Phlox kelseyi* 'Lemhi Midnight' (not patented). 'Betty Blake' is similar to 'Violet Pinwheels' in having cleft petals and violet striae. 'Betty Blake' differs from 'Violet Pinwheels' in having irregularly shaped floral eyes that are white in color, in having deeply cleft narrow petals with sharply pointed apices, in having leaves that are longer in length, and in having petals that are irregularly placed and flattened into a single plane. 'Lemhi Midnight' is similar to 'Violet Pinwheels' in having leaves that are lanceolate in shape and no longer than 1.8 cm in length and in having a repeat bloom period from late summer into autumn. 'Lemhi Midnight' differs from 'Violet Pinwheels' in having broadly obovate petals that are overlapping, in having a large floral eye that is white in color with no floral striae, and in having a very low creeping mat habit that is shorter in height.

BRIEF DESCRIPTION OF THE DRAWINGS

The accompanying colored photographs illustrate the overall appearance and distinct characteristics of the new *Phlox*. The photographs were taken in June of two year-old plants of 'Violet Pinwheels' as grown in a trial garden in Glencoe, Ill.

The photograph in FIG. 1 provides an overall view of the plant habit of 'Violet Pinwheels' in bloom.

Figure 1:
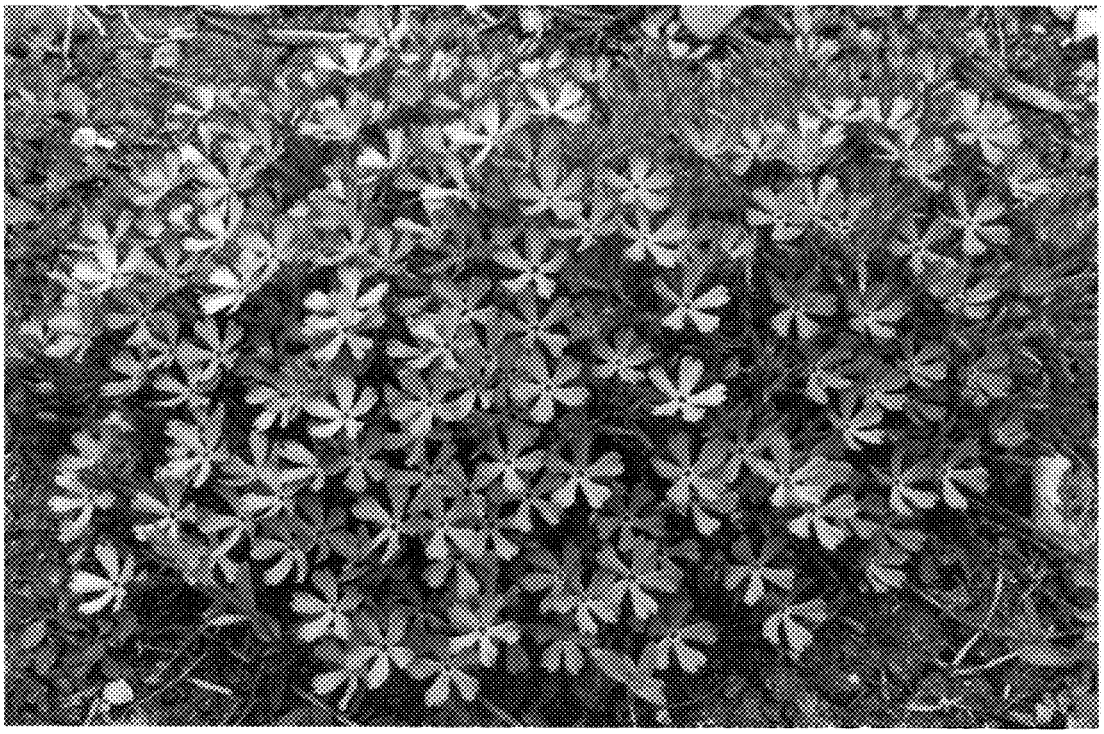
Figure 2:
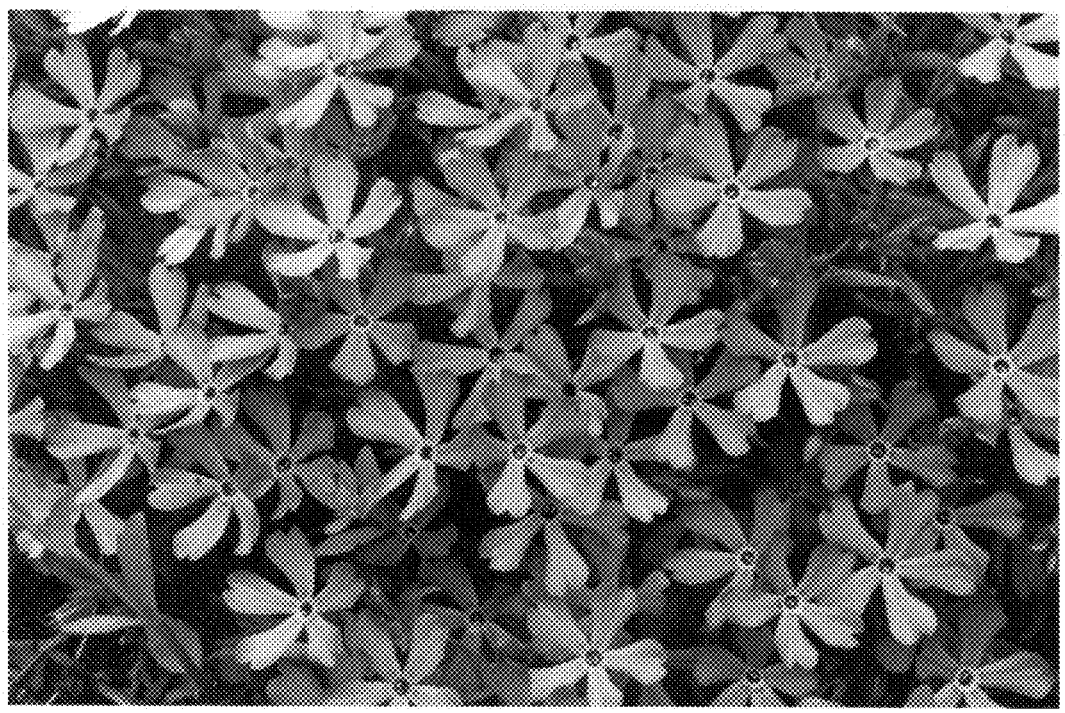

The Photograph in FIG. 2 provides a close-up view of the flowers of 'Violet Pinwheels'

The colors in the photograph may differ slightly from the color values cited in the detailed botanical description, which accurately describe the colors of the new *Phlox*.

DETAILED BOTANICAL DESCRIPTION OF THE PLANT

The following is a detailed description of two year-old plants (three year-old plants for mature size) of the new cultivar as grown in a trial garden in Glencoe, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms for four to six weeks beginning in early to mid April and continuing into mid May and light repeat blooms from August through October in northern Illinois.

*Plant habit*.—Low, spreading mounded herbaceous perennial.

*Height and spread*.—An average of 10 cm in height and 48 cm in width (3 year-old plant).

*Hardiness*.—At least hardy in U.S.D.A. Zones 4 to 7.

*Diseases and pests*.—Resistance to powdery mildew has been observed.

*Root description*.—Fibrous.

*Growth rate*.—Vigorous.

*Propagation*.—Tip stem cuttings (from vegetative growth).

Stem description:

*Stem size*.—Main stems, an average of 10 cm in length and 2 mm in width, lateral stems; variable, up to 10 cm in length and 1.5 mm in width.

*Stem shape*.—Oval.

*Stem strength*.—Strong.

*Stem color*.—145B with some portions slightly diffused with N77A.

*Stem surface*.—Glabrous, slightly glossy, covered with very small wooly dense pubescent hairs 1 mm in length and too short to measure with R.H.S. Colour Chart.

*Stem aspect*.—Held at different ranges from nearly upright to hanging.

*Internode length*.—An average of 1 cm.

*Branching habit*.—An average of 20 stems per plant one year in age, an average of 3 lateral branches per main stem.

Foliage description:

*Leaf shape*.—Narrowly elliptic.

*Leaf division*.—Simple.

*Leaf base*.—Attenuate.

*Leaf apex*.—Acute acuminate.

*Leaf venation*.—Pinnate, not conspicuous, matches leaf color on upper and lower surfaces.

*Leaf margins*.—Entire.

*Leaf attachment*.—Sessile.

*Leaf arrangement*.—Opposite.

*Leaf surface*.—Glabrous, dull and sparsely covered in fine wooly pubescence 0.5 mm in length and too small to measure with R.H.S. Colour Chart on upper and lower surface.

*Leaf color*.—Upper and lower surface young foliage; 144A, upper and lower surface mature; 137B.

*Leaf size*.—Up to 1.8 cm in length and 2 mm in width.

*Leaf quantity*.—An average of 16 on a stem.

*Leaf fragrance*.—None.

Flower description:

*Inflorescence type*.—One to three floral buds on axillary and terminal shoots.

*Lastingness of inflorescence*.—Individual flower lasts about 3 days.

*Flower fragrance*.—None detected.

*Flower number*.—One to three per flowering shoot.

*Flower aspect*.—Upright to outward, cupped with petals turned in.

*Flower bud*.—An average of 1.6 cm in length and 3 mm in width, apex is conical in shape with base linear (tube portion), apex is a blend of N88A and N88B in color, tube portion is a blend of N88B and N88C and enclosed by calyx that is a blend of 138A and 138B in color.

*Flower form*.—Salviform.

*Flower size*.—An average of 1.6 cm in height and 2.0 cm in diameter (average based on ten flowers from plants in ground).

*Corolla tube* (*both surfaces*).—About 8 mm in length, 1.7 mm in width, a blend of N88B and N88C in color, glabrous and satiny surface, mature to N87B to N87D.

*Corolla lobes*.—5, obcordate-obovate with narrow base in shape, held as open campanulate and slightly turned inward when fully open, not overlapping, about 9 mm in length and 4 mm width, cordate to single notched apex, base cuneate and fused to tube, entire margins, upper and lower surface color when opening N88B with an eye around the throat of the tube 85D and paired striae adjacent to the eye of 86A, upper and lower surface color when mature N87B to N87D.

*Calyx*.—Closed campanulate in form, lower 50% fused, sepals with lanceolate shaped sepal tips.

*Sepals*.—5, 50% fused with free tips, linear in shape with lanceolate shaped tips, margins entire, base fused, apex narrowly apiculate, an average of 1 cm in length and 0.7 mm in width, inner and outer surface is pubescent, color on inner and outer surface 138A and 138B.

*Peduncles*.—Oval in shape, an average of 1 cm in length and 0.8 mm in width, held at primarily upright from node, pubescent surface, color 138B.

*Pedicels*.—None, single flowers.

Reproductive organs:

*Gynoecium.*—1 pistil, stigma is tri-fid, 1 mm in length and 151D in color, style is about 7 mm in length, very fine and 145D in color, ovary is superior, oblong in shape, about 1.5 mm in length and 1 mm in width and 144A in color.

*Androcoecium.*—5 stamens, anthers are basifixed, oblong in shape, and 1 mm in length, filaments are adnate to petal tube portion, about 0.5 mm in width and N88D in color, pollen is abundant in quantity and 22A in color.

*Seeds.*—Seed production has not been observed, presumed sterile.

It is claimed:

1. A new and distinct cultivar of *Phlox* plant named 'Violet Pinwheels' as herein illustrated and described.

* * * * *